(12) United States Patent
Safaei-Ghomi et al.

(10) Patent No.: US 11,155,516 B2
(45) Date of Patent: Oct. 26, 2021

(54) SYNTHESIS OF 2-(2-AMINOETHOXY) ETHANOL

(71) Applicants: Javad Safaei-Ghomi, Qom (IR); Mansoureh Naderi, Parand New Town (IR)

(72) Inventors: Javad Safaei-Ghomi, Qom (IR); Mansoureh Naderi, Parand New Town (IR)

( * ) Notice: Subject to any disclaimer, the term of this patent is extended or adjusted under 35 U.S.C. 154(b) by 0 days.

(21) Appl. No.: 17/069,079

(22) Filed: Oct. 13, 2020

(65) Prior Publication Data

US 2021/0040029 A1 Feb. 11, 2021

Related U.S. Application Data

(60) Provisional application No. 62/914,568, filed on Oct. 14, 2019.

(51) Int. Cl.
*C07C 213/02* (2006.01)
*C07C 213/10* (2006.01)
*C07C 215/08* (2006.01)

(52) U.S. Cl.
CPC .......... *C07C 213/02* (2013.01); *C07C 213/10* (2013.01); *C07C 215/08* (2013.01)

(58) Field of Classification Search
None
See application file for complete search history.

(56) References Cited

FOREIGN PATENT DOCUMENTS

CN 104262173 * 1/2015

OTHER PUBLICATIONS

Thomson Reuters abstractor Fan et al. (CN 104262173, pub date Jan. 7, 2015) (Year: 2015).*
English translation of Fan et al. Chinese CN 104262173, pub year 2015 (Year: 2015).*

* cited by examiner

*Primary Examiner* — Sudhakar Katakam
*Assistant Examiner* — Jennifer C Sawyer
(74) *Attorney, Agent, or Firm* — Bajwa IP Law Firm; Haris Zaheer Bajwa

(57) ABSTRACT

A method for synthesizing 2-(2-aminoethoxy) ethanol, including the steps of producing 2-(2-phthalimidoethoxy) ethanol by reacting 5-tosyloxy-3-oxapentanol with potassium phthalate and converting the 2-(2-phthalimidoethoxy) ethanol to the 2-(2-aminoethoxy) ethanol by reacting the 2-(2-phthalimidoethoxy) ethanol with hydrazine monohydrate. Reacting the 2-(2-phthalimidoethoxy) ethanol with the hydrazine monohydrate may include forming a final mixture by adding the hydrazine monohydrate to a solution of 2-(2-phthalimidoethoxy) ethanol, refluxing the final mixture in a nitrogen atmosphere, extracting a second organic phase containing the 2-(2-aminoethoxy) ethanol from the final mixture using a second portion of chloroform, and purifying the 2-(2-aminoethoxy) ethanol from the second organic phase.

18 Claims, 20 Drawing Sheets

SYNTHESIS OF 2-(2-AMINOETHOXY) ETHANOL

CROSS-REFERENCE TO RELATED APPLICATION

This application claims the benefit of priority from U.S. Provisional Patent Application Ser. No. 62/914,568, filed on Oct. 14, 2019, and entitled "A METHOD FOR SYNTHESIS OF 2-(2-AMINOETHOXY) ETHANOL," which is incorporated herein by reference in its entirety.

TECHNICAL FIELD

The present disclosure generally relates to 2-(2-aminoethoxy) ethanol, particularly to a method for synthesizing 2-(2-aminoethoxy) ethanol, and more particularly to a method for synthesizing 2-(2-aminoethoxy) ethanol using the Gabriel synthesis.

BACKGROUND

Diglycolamine or 2-(2-aminoethoxy) ethanol is a versatile amine generally used in stripper solutions for applications in electronics, and as a solvent to remove corrosive acid gases, such as hydrogen sulfide, carbon dioxide, and carbonyl sulfides in gas purification units of oil industry. Also, 2-(2-aminoethoxy) ethanol may be used for preparation of foam stabilizers, humidifying agents, emulsifiers, corrosion inhibitors, and coloring agents.

However, synthesis of the 2-(2-aminoethoxy) ethanol faces several challenges. For example, conventional methods for producing 2-(2-aminoethoxy) ethanol require expensive homogenous or heterogeneous catalysts such as palladium, hard and dangerous reaction conditions, such as using hydrogen gas, high temperature, and high pressure, that limit industrial applicability of the conventional methods. Also, yield of the conventional methods is generally low due to the production of several byproducts.

Hence, there is a need for a cost-effective method for the synthesis of 2-(2-aminoethoxy) ethanol using low-cost raw materials with safe reaction conditions without any need for hydrogen gas, high temperature, and high pressure. Moreover, there is a need for an efficient method for producing the 2-(2-aminoethoxy) ethanol with high yield by preventing the formation of byproducts.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for synthesizing 2-(2-aminoethoxy) ethanol. In an exemplary embodiment, the method may include producing 2-(2-phthalimidoethoxy) ethanol by reacting 5-tosyloxy-3-oxapentanol with potassium phthalate and converting the 2-(2-phthalimidoethoxy) ethanol to the 2-(2-aminoethoxy) ethanol by reacting the 2-(2-phthalimidoethoxy) ethanol with hydrazine monohydrate. In an exemplary embodiment, reacting the 2-(2-phthalimidoethoxy) ethanol with the hydrazine monohydrate may include forming a final mixture by adding the hydrazine monohydrate to a solution of 2-(2-phthalimidoethoxy) ethanol, refluxing the final mixture in a nitrogen atmosphere, extracting a second organic phase containing the 2-(2-aminoethoxy) ethanol from the final mixture using a second portion of chloroform, and purifying the 2-(2-aminoethoxy) ethanol from the second organic phase.

In an exemplary embodiment, refluxing the final mixture in the nitrogen atmosphere may include refluxing the final mixture in the nitrogen atmosphere for a time period between about 20 hours and about 26 hours. In an exemplary embodiment, refluxing the final mixture in the nitrogen atmosphere may include refluxing the final mixture at a temperature between 85° C. and 95° C. In an exemplary embodiment, the solution of 2-(2-phthalimidoethoxy) ethanol may have a concentration between about 0.042 M and about 0.045 M in absolute ethanol. In an exemplary embodiment, adding the hydrazine monohydrate to the solution of the 2-(2-phthalimidoethoxy) ethanol may include adding the hydrazine monohydrate with a volume concentration between about 13% and about 14.3% (v/v) to the solution of the 2-(2-phthalimidoethoxy) ethanol.

In an exemplary embodiment, extracting the 2-(2-aminoethoxy) ethanol from the final mixture using the second portion of chloroform may include adding the second portion of chloroform to the final mixture at room temperature. In an exemplary embodiment, adding the second portion of chloroform to the final mixture may include adding the second portion of chloroform to the final mixture with a ratio of the 2-(2-phthalimidoethoxy) ethanol to the second portion of chloroform between about 0.0100 mol/L and about 0.0108 mol/L. In an exemplary embodiment, adding the second portion of chloroform to the final mixture may include adding the second portion of chloroform to the final mixture until no precipitate is formed in the final mixture.

In an exemplary embodiment, reacting the 5-tosyloxy-3-oxapentanol with the potassium phthalate may include forming a reaction mixture by adding the 5-tosyloxy-3-oxapentanol and the potassium phthalate to dry dimethylformamide (DMF), refluxing the reaction mixture in a nitrogen atmosphere, extracting a first organic phase containing the 2-(2-phthalimidoethoxy) ethanol from the reaction mixture using a first portion of chloroform, and purifying the 2-(2-phthalimidoethoxy) ethanol from the first organic phase.

In an exemplary embodiment, extracting the 2-(2-phthalimidoethoxy) ethanol from the reaction mixture using the first portion of chloroform may include adding the first portion of chloroform to the reaction mixture at room temperature. In an exemplary embodiment, refluxing the reaction mixture in the nitrogen atmosphere may include refluxing the reaction mixture in the nitrogen atmosphere for a time period between about 18 hours and about 22 hours. In an exemplary embodiment, refluxing the reaction mixture in the nitrogen atmosphere may include refluxing the reaction mixture at a temperature between about 170° C. and about 190° C. In an exemplary embodiment, adding the 5-tosyloxy-3-oxapentanol and the potassium phthalate to the dry DMF may include adding the 5-tosyloxy-3-oxapentanol and the potassium phthalate to the dry DMF with a molar ratio of the 5-tosyloxy-3-oxapentanol to the potassium phthalate between about 0.4 and about 0.6.

In an exemplary embodiment, adding the 5-tosyloxy-3-oxapentanol and the potassium phthalate to the dry DMF may include adding the 5-tosyloxy-3-oxapentanol with a concentration between about 0.13 M and about 0.17 M to the dry DMF. In an exemplary embodiment, adding the 5-tosyloxy-3-oxapentanol and the potassium phthalate to the dry DMF may include adding the potassium phthalate with a concentration between about 0.28 M and about 0.32 M to the dry DMF. In an exemplary embodiment, an exemplary method for synthesizing 2-(2-aminoethoxy) ethanol may further include forming the 5-tosyloxy-3-oxapentanol by reacting p-toluenesulfonyl chloride with diethylene glycol. In an exemplary embodiment, purifying the 2-(2-aminoethoxy) ethanol from the second organic phase may include isolating the 2-(2-aminoethoxy) ethanol from the second organic phase using a column chromatography technique.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Disclosed herein is an exemplary cost-effective and straightforward method for synthesizing 2-(2-aminoethoxy) ethanol without requiring expensive catalysts like palladium. In an exemplary method, Gabriel synthesis may be used for synthesizing 2-(2-aminoethoxy) ethanol, which may not only decrease the costs of the conventional methods but may also obviate the need for high temperature and high pressure, which may be considered as industrial obstacles. An exemplary method may be considered as an efficient method for synthesis of 2-(2-aminoethoxy) ethanol with high purity by extracting the 2-(2-aminoethoxy) ethanol through precipitating byproducts using chloroform.

Figure 1A:
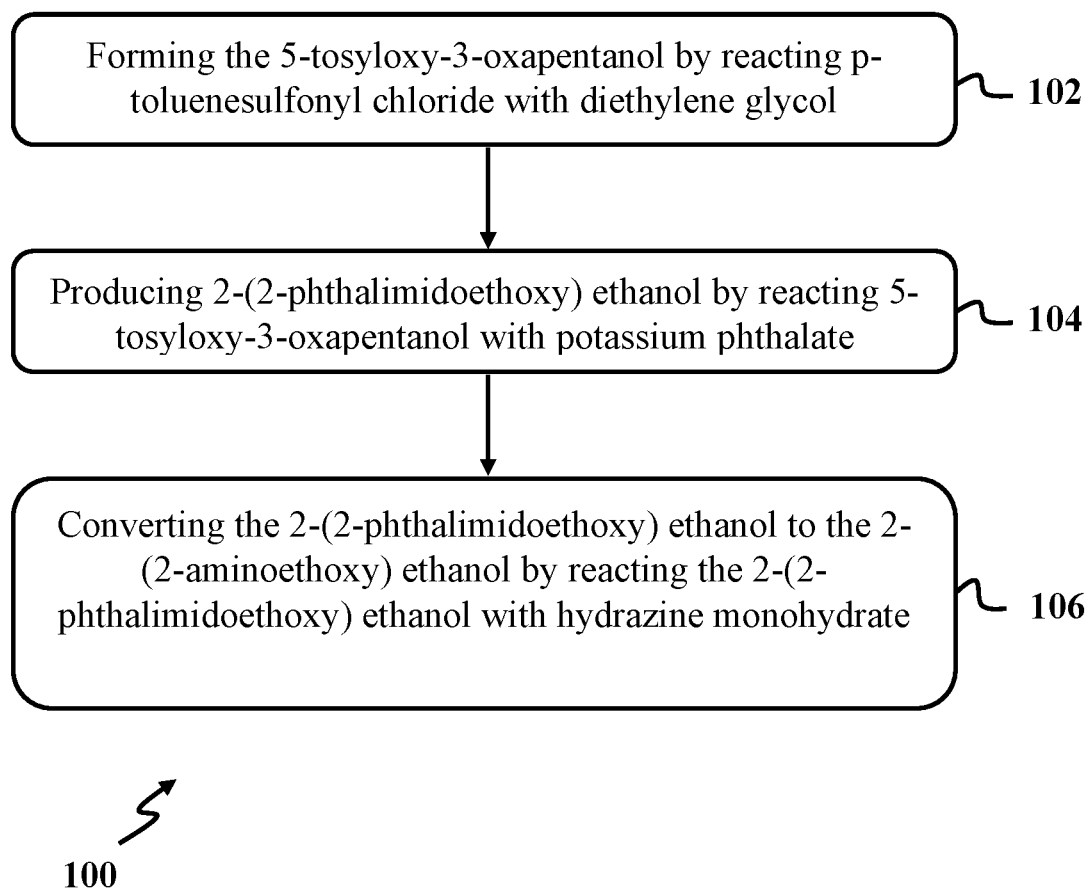
FIG. 1A shows a flowchart of an exemplary method for synthesizing 2-(2-aminoethoxy) ethanol, consistent with one or more exemplary embodiments of the present disclosure.

FIG. 1A shows a flowchart of an exemplary method 100 for synthesizing 2-(2-aminoethoxy) ethanol, consistent with one or more exemplary embodiments of the present disclosure. An exemplary method 100 may include forming the 5-tosyloxy-3-oxapentanol by reacting p-toluenesulfonyl chloride with diethylene glycol (step 102), producing 2-(2-phthalimidoethoxy) ethanol by reacting 5-tosyloxy-3-oxapentanol with potassium phthalate (step 104), and converting the 2-(2-phthalimidoethoxy) ethanol to the 2-(2-aminoethoxy) ethanol by reacting the 2-(2-phthalimidoethoxy) ethanol with hydrazine monohydrate (step 106).

Figure 2A:
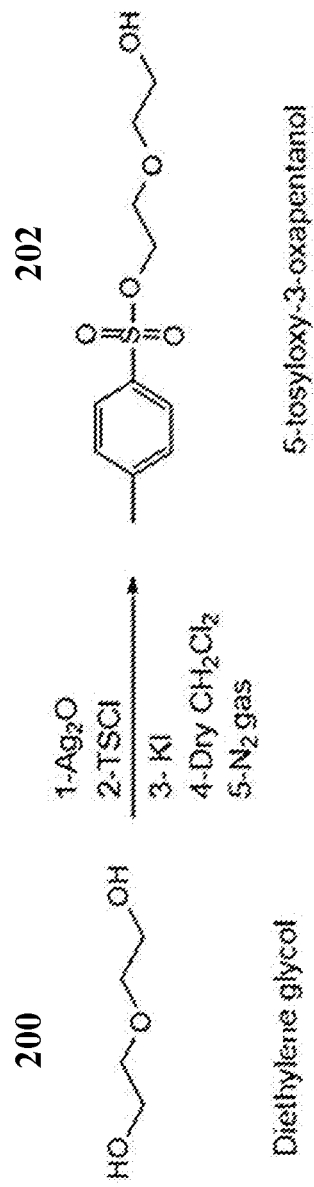
FIG. 2A illustrates a schematic representation for forming 5-tosyloxy-3-oxapentanol by reacting p-toluenesulfonyl chloride with diethylene glycol, consistent with one or more exemplary embodiments of the present disclosure.

In further detail with respect to step 102, in an exemplary embodiment, forming the 5-tosyloxy-3-oxapentanol may include reacting p-toluenesulfonyl chloride (TSCl) with diethylene glycol. FIG. 2A illustrates a schematic representation of step 102 for forming 5-tosyloxy-3-oxapentanol 202 reacting TSCl with diethylene glycol 200, consistent with one or more exemplary embodiments of the present disclosure. In an exemplary embodiment, reacting the TSCl with diethylene glycol 200 may include adding a tosyl group to the diethylene glycol 200.

Figure 1B:
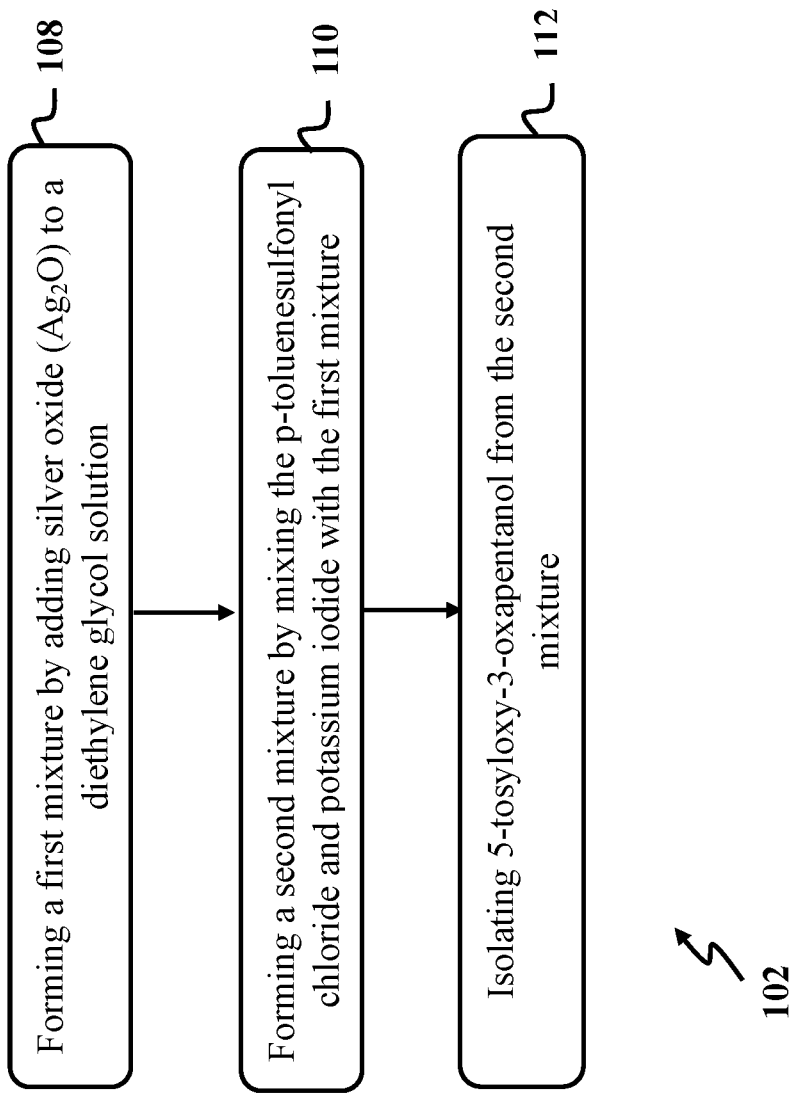
FIG. 1B shows a flowchart of an exemplary method for forming the 5-tosyloxy-3-oxapentanol by reacting p-toluenesulfonyl chloride (TSCl) with diethylene glycol, consistent with one or more exemplary embodiments of the present disclosure.

FIG. 1B shows a flowchart of an exemplary method for forming 5-tosyloxy-3-oxapentanol by reacting TSCl with diethylene glycol, consistent with one or more exemplary embodiments of the present disclosure. Referring to FIG. 1B, details of exemplary step 102 of method 100 may include forming a first mixture by adding silver oxide ($Ag_2O$) to a diethylene glycol solution (step 108), forming a second mixture by mixing the TSCl and potassium iodide (KI) with the first mixture (step 110), and isolating 5-tosyloxy-3-oxapentanol from the second mixture (step 112).

In further detail with respect to step 108, forming a first mixture may include mixing $Ag_2O$ with a diethylene glycol solution. In an exemplary embodiment, mixing the $Ag_2O$ with the diethylene glycol solution may entail stirring the $Ag_2O$ with the diethylene glycol solution. In an exemplary embodiment, the diethylene glycol solution may have a concentration between about 0.093 M and about 0.107 M in dry dichloromethane ($CH_2Cl_2$). In an exemplary embodiment, mixing the $Ag_2O$ with the diethylene glycol solution may include mixing $Ag_2O$ with a final concentration between about 0.146 M and about 0.160 M with a diethylene glycol solution. In an exemplary embodiment, mixing the $Ag_2O$ with the diethylene glycol solution may include mixing the $Ag_2O$ with the diethylene glycol solution at a temperature of about 0° C. in a nitrogen atmosphere for a time period between about 45 minutes and about 75 minutes.

In further detail with respect to step 110, forming a second mixture may include mixing the TSCl and KI with the first mixture. In an exemplary embodiment, mixing the TSCl and the KI with the first mixture may entail stirring the TSCl and the KI with the first mixture. In an exemplary embodiment, mixing the TSCl and the KI with the first mixture may include mixing the TSCl with a final concentration between about 0.103 M and about 0.117 M and the KI with a final concentration between about 0.013 M and about 0.026 M with the exemplary first mixture that may be formed utilizing exemplary step 108. In an exemplary embodiment, mixing the TSCl and KI with the first mixture may include mixing the TSCl and KI with the first mixture at a temperature of about 0° C. in a nitrogen atmosphere for a time period between about 3 hours and about 5 hours.

In further detail with respect to step 112, isolating 5-tosyloxy-3-oxapentanol from the second mixture may include purifying the 5-tosyloxy-3-oxapentanol as a colorless oil from the second mixture using chromatography. In an exemplary embodiment, purifying the 5-tosyloxy-3-oxapentanol from the second mixture using chromatography may include purifying the 5-tosyloxy-3-oxapentanol from the second mixture using column chromatography on silica gel.

Figure 2B:
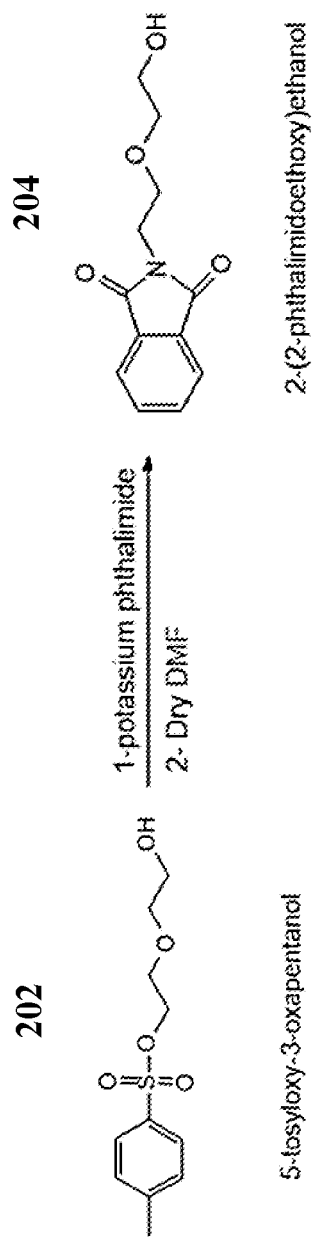
FIG. 2B illustrates a schematic representation for producing 2-(2-phthalimidoethoxy) ethanol by reacting the 5-tosyloxy-3-oxapentanol with potassium phthalate, consistent with one or more exemplary embodiments of the present disclosure.

Referring back to FIG. 1A, in further detail with respect to step 104, in an exemplary embodiment, producing 2-(2-phthalimidoethoxy) ethanol may include reacting 5-tosyloxy-3-oxapentanol with potassium phthalate. FIG. 2B illustrates a schematic representation of step 104 for synthesizing 2-(2-phthalimidoethoxy) ethanol 204 by reacting the 5-tosyloxy-3-oxapentanol 202 with potassium phthalate, consistent with one or more exemplary embodiments of the present disclosure.

Figure 1C:
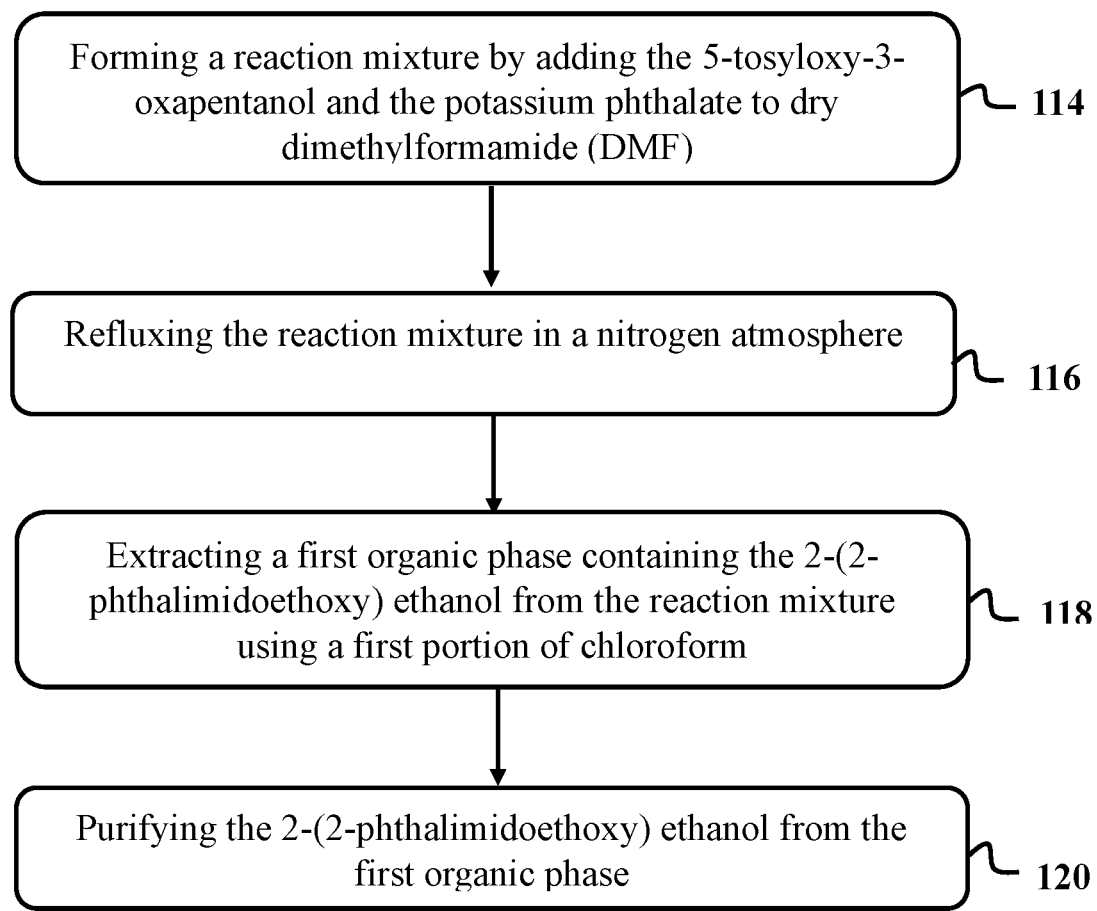
FIG. 1C shows a flowchart of an exemplary method for producing 2-(2-phthalimidoethoxy) ethanol by reacting 5-tosyloxy-3-oxapentanol with potassium phthalate, consistent with one or more exemplary embodiments of the present disclosure.

FIG. 1C shows a flowchart of an exemplary method for producing 2-(2-phthalimidoethoxy) ethanol by reacting 5-tosyloxy-3-oxapentanol with potassium phthalate, consistent with one or more exemplary embodiments of the present disclosure. Referring to FIG. 1C, details of exemplary step 104 of method 100 may include forming a reaction mixture by adding the 5-tosyloxy-3-oxapentanol and the potassium phthalate to dry dimethylformamide (DMF) (step 114), refluxing the reaction mixture in a nitrogen atmosphere (step 116), extracting a first organic phase containing the 2-(2-phthalimidoethoxy) ethanol from the reaction mixture using a first portion of chloroform (step 118), and purifying the 2-(2-phthalimidoethoxy) ethanol from the first organic phase (step 120).

In further detail with respect to step 114, in an exemplary embodiment, forming a reaction mixture may include adding the 5-tosyloxy-3-oxapentanol and the potassium phthalate to dry DMF. In an exemplary embodiment, adding the 5-tosyloxy-3-oxapentanol and the potassium phthalate to the dry DMF may include adding the 5-tosyloxy-3-oxapentanol and the potassium phthalate to the dry DMF with a molar ratio of the 5-tosyloxy-3-oxapentanol to the potassium phthalate between about 0.4 and about 0.6. In an exemplary embodiment, adding the 5-tosyloxy-3-oxapentanol and the potassium phthalate to the dry DMF may include adding the 5-tosyloxy-3-oxapentanol with a concentration between about 0.13 M and about 0.17 M to the dry DMF. In an exemplary embodiment, adding the 5-tosyloxy-3-oxapentanol and the potassium phthalate to the dry DMF may include adding the potassium phthalate with a concentration between about 0.28 M and about 0.32 M to the dry DMF.

In further detail with respect to step 116, in an exemplary embodiment, refluxing the reaction mixture in a nitrogen atmosphere may include distilling the reaction mixture in the nitrogen atmosphere for a time period between about 18 hours and about 22 hours. In an exemplary embodiment, refluxing the reaction mixture in the nitrogen atmosphere may include distilling the reaction mixture at a temperature between about 170° C. and about 190° C.

In further detail with respect to step 118, in an exemplary embodiment, extracting a first organic phase containing the 2-(2-phthalimidoethoxy) ethanol from the reaction mixture using a first portion of chloroform may include adding the first portion of chloroform to the reaction mixture at room temperature. In an exemplary embodiment, extracting the first organic phase from the reaction mixture may include extracting the first organic phase from the reaction mixture by adding the first portion of chloroform to the reaction mixture in a decanter.

In further detail with respect to step 120, in an exemplary embodiment, purifying the 2-(2-phthalimidoethoxy) ethanol from the first organic phase may include purifying the 2-(2-phthalimidoethoxy) ethanol from the first organic phase using a column chromatography technique. In an exemplary embodiment, purifying the 2-(2-phthalimidoethoxy) ethanol from the first organic phase using a column chromatography technique may include using a solvent including n-hexane and ethyl acetate with a ratio of about 3:7.

Figure 2C:
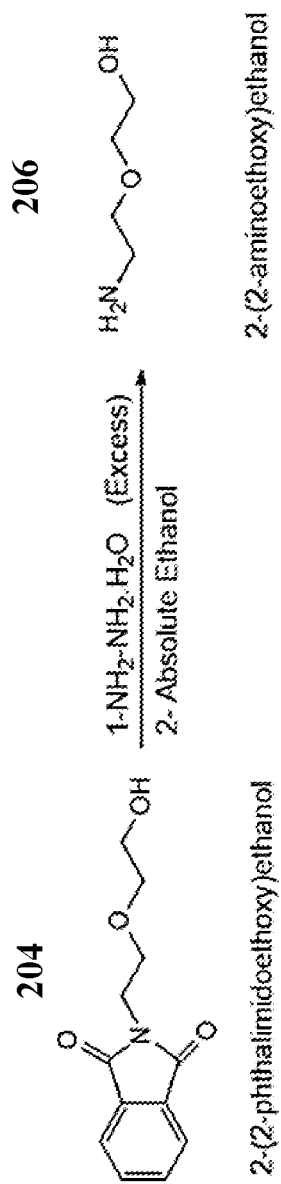
FIG. 2C illustrates a schematic representation for converting the 2-(2-phthalimidoethoxy) ethanol to the 2-(2-aminoethoxy) ethanol by reacting the 2-(2-phthalimidoethoxy) ethanol with hydrazine monohydrate, consistent with one or more exemplary embodiments of the present disclosure.

Referring back to FIG. 1A, in further detail with respect to step 106, in an exemplary embodiment, converting the 2-(2-phthalimidoethoxy) ethanol to the 2-(2-aminoethoxy) ethanol may include reacting the 2-(2-phthalimidoethoxy) ethanol with hydrazine monohydrate. FIG. 2C illustrates a schematic representation of step 106 for reacting the 2-(2-phthalimidoethoxy) ethanol 204 with hydrazine monohydrate ($NH_2$—$NH_2.H_2O$), consistent with one or more exemplary embodiments of the present disclosure.

Figure 1D:
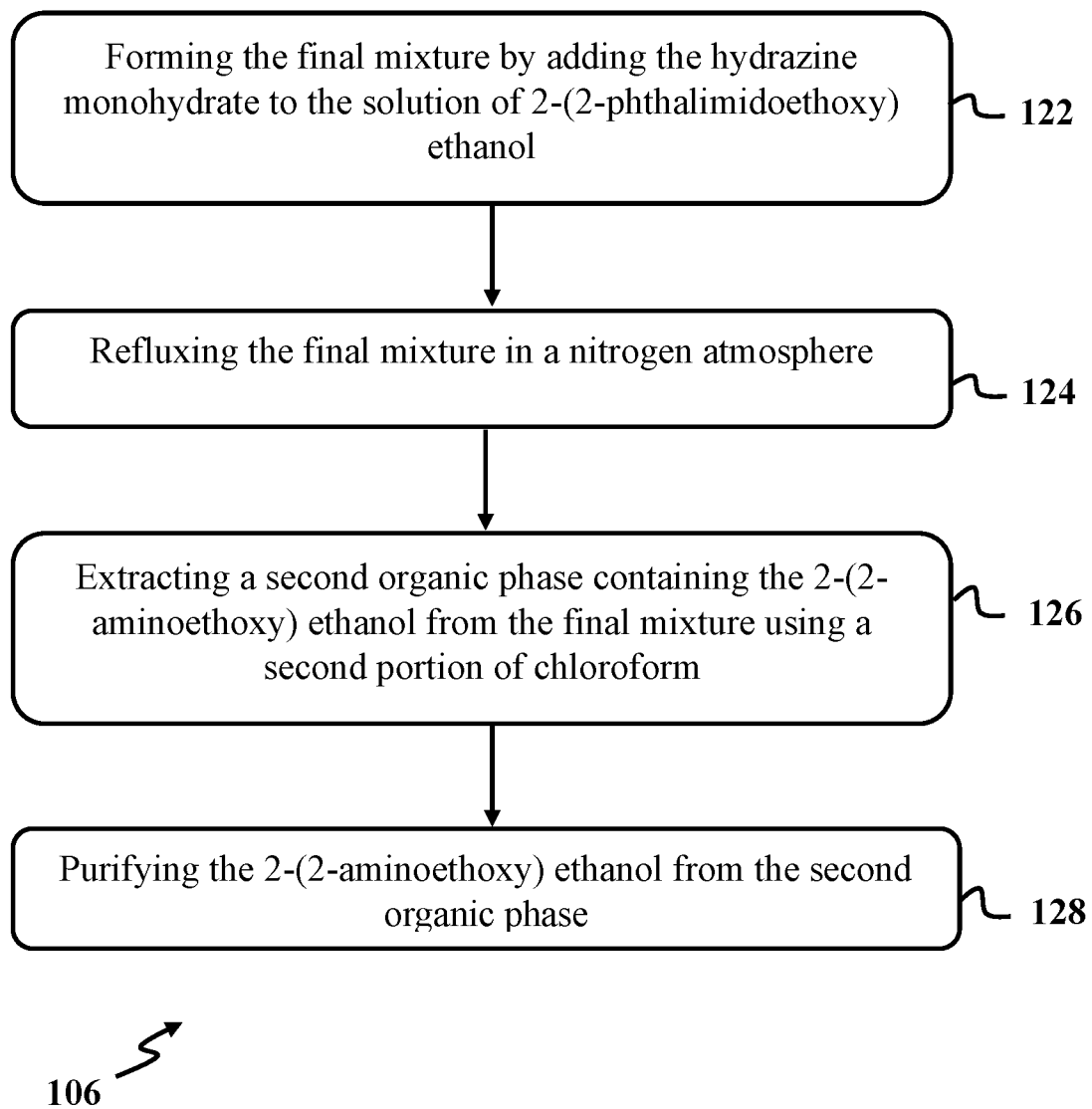
FIG. 1D shows a flowchart of an exemplary method for converting the 2-(2-phthalimidoethoxy) ethanol to the 2-(2-aminoethoxy) ethanol by reacting the 2-(2-phthalimidoethoxy) ethanol with hydrazine monohydrate, consistent with one or more exemplary embodiments of the present disclosure.

FIG. 1D shows a flowchart of an exemplary method for converting the 2-(2-phthalimidoethoxy) ethanol 204 to the 2-(2-aminoethoxy) ethanol 206 by reacting the 2-(2-phthalimidoethoxy) ethanol 204 with hydrazine monohydrate, consistent with one or more exemplary embodiments of the present disclosure. Referring to FIG. 1D, details of exemplary step 106 of method 100 may include forming the final mixture by adding the hydrazine monohydrate to the solution of 2-(2-phthalimidoethoxy) ethanol (step 122), refluxing the final mixture in a nitrogen atmosphere (step 124), extracting a second organic phase containing the 2-(2-aminoethoxy) ethanol from the final mixture using a second portion of chloroform (step 126), and purifying the 2-(2-aminoethoxy) ethanol from the second organic phase (step 128).

In further detail with respect to step 122, in an exemplary embodiment, forming the final mixture may include adding the hydrazine monohydrate to the solution of 2-(2-phthalimidoethoxy) ethanol. In an exemplary embodiment, the solution of 2-(2-phthalimidoethoxy) ethanol may have a concentration between about 0.042 M and about 0.045 M in absolute ethanol. In an exemplary embodiment, adding the hydrazine monohydrate to the solution of the 2-(2-phthalimidoethoxy) ethanol may include adding the hydrazine monohydrate with a volume concentration between about 13% and about 14.3% (v/v) to the solution of the 2-(2-phthalimidoethoxy) ethanol.

In further detail with respect to step 124, in an exemplary embodiment, refluxing the final mixture in a nitrogen atmosphere may include refluxing the final mixture in the nitrogen atmosphere for a time period between about 20 hours and about 26 hours. In an exemplary embodiment, refluxing the final mixture in the nitrogen atmosphere may include refluxing the final mixture at a temperature between about 85° C. and about 95° C.

In further detail with respect to step 126, in an exemplary embodiment, extracting a second organic phase containing the 2-(2-aminoethoxy) ethanol from the final mixture using a second portion of chloroform may include adding the second portion of chloroform to the final mixture at room temperature. In an exemplary embodiment, adding the second portion of chloroform to the final mixture may include adding the second portion of chloroform to the final mixture with a ratio of the 2-(2-phthalimidoethoxy) ethanol to the second portion of chloroform between about 0.0100 mol/L and about 0.0108 mol/L. In an exemplary embodiment, adding the second portion of chloroform to the final mixture may include adding the second portion of chloroform to the final mixture until no precipitate is formed in the final mixture. In an exemplary embodiment, adding the second portion of chloroform to the final mixture may separate the 2-(2-aminoethoxy) ethanol by precipitating different byproducts such as several compounds derived from 2-(2-phthalimidoethoxy) ethanol.

In further detail with respect to step 128, in an exemplary embodiment, purifying the 2-(2-aminoethoxy) ethanol from the second organic phase may include isolating the 2-(2-aminoethoxy) ethanol from the second organic phase using a column chromatography technique. In an exemplary embodiment, purifying the 2-(2-aminoethoxy) ethanol from the second organic phase using a column chromatography technique may include isolating the 2-(2-aminoethoxy) ethanol from the second organic phase using a solvent including n-hexane and ethyl acetate with a ratio of about 3:7.

EXAMPLES

Example 1: Forming 5-Tosyloxy-3-Oxapentanol Using Diethylene Glycol

In this example, 5-tosyloxy-3-oxapentanol was formed by reacting p-toluenesulfonyl chloride with diethylene glycol utilizing a process similar to step 102 of exemplary method 100 as presented in FIG. 1. At first, a solution of diethylene glycol with a concentration of about 0.1 M was formed by dissolving about 1.5 mmol of diethylene glycol in about 15 ml of dry dichloromethane ($CH_2Cl_2$) in a round bottom flask. The solution of diethylene glycol was cooled to a temperature of about 0° C. using an ice-salt bath under nitrogen.

In the next step, a first mixture was formed by mixing freshly prepared silver (I) oxide as a catalyst with a final concentration of about 0.15 M with the solution of diethylene glycol for a time period of about 1 hour. Then, a second solution was formed by adding p-toluenesulfonyl chloride (about 1.65 mmol) with a concentration of about 0.11 and potassium iodide (about 0.3 mmol) with a concentration of about 0.02 to the first mixture. The second solution was stirred at a temperature of about 0° C. in an ice-salt bath under nitrogen for a time period of about 4 hours. In the second mixture, the 5-tosyloxy-3-oxapentanol was formed by tosylation of the diethylene glycol using p-toluenesulfonyl chloride.

In order to isolate the 5-tosyloxy-3-oxapentanol from the second mixture, the second mixture was filtered using a filter paper and washed with 40 ml of ethyl acetate to form a filtrate. The filtrate was dried over anhydrous magnesium sulfate. Then, $CH_2Cl_2$, as the solvent, was evaporated utilizing a rotary evaporator. In the end, the crude product was purified by column chromatography on silica gel using a solution, including n-hexane and ethyl acetate, with a ratio of about 3:7. As a result, the 5-tosyloxy-3-oxapentanol with an amount of about 0.32 grams was obtained as a colorless oil with a yield of about 82%.

Figure 3A:
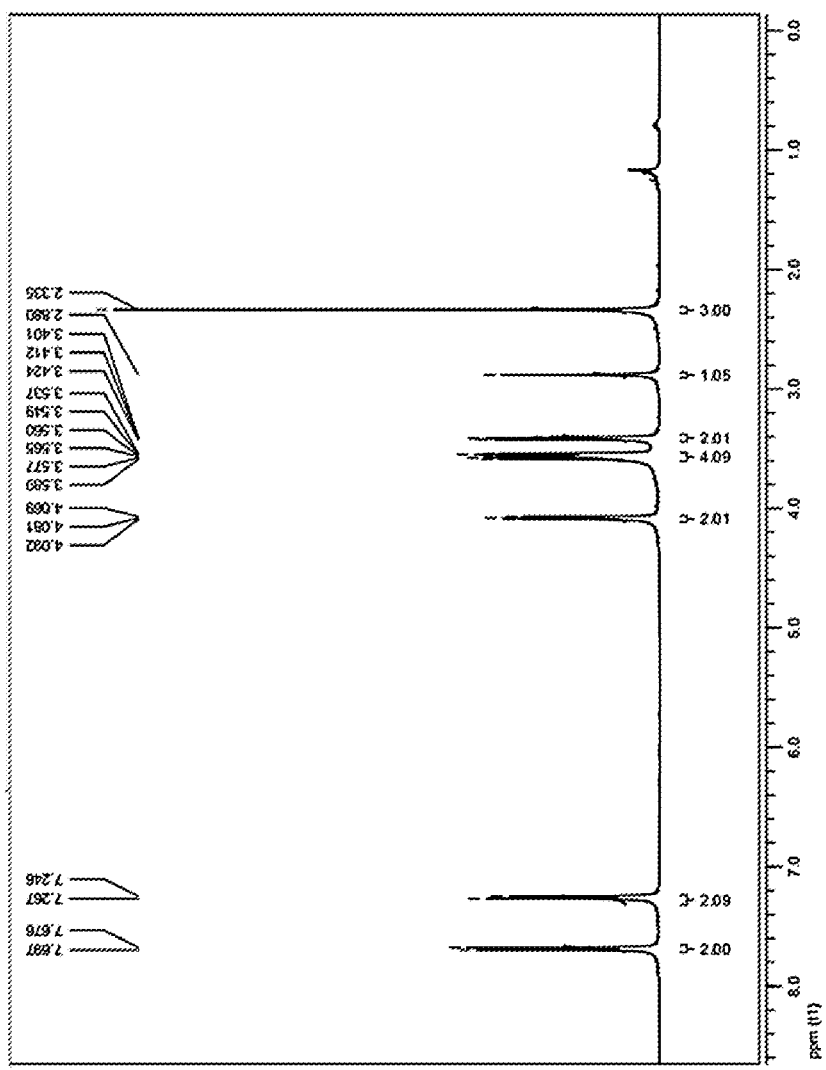
FIG. 3A illustrates a proton nuclear magnetic resonance ($^1$H NMR) spectrum of 5-tosyloxy-3-oxapentanol, consistent with one or more exemplary embodiments of the present disclosure.
Figure 3B:
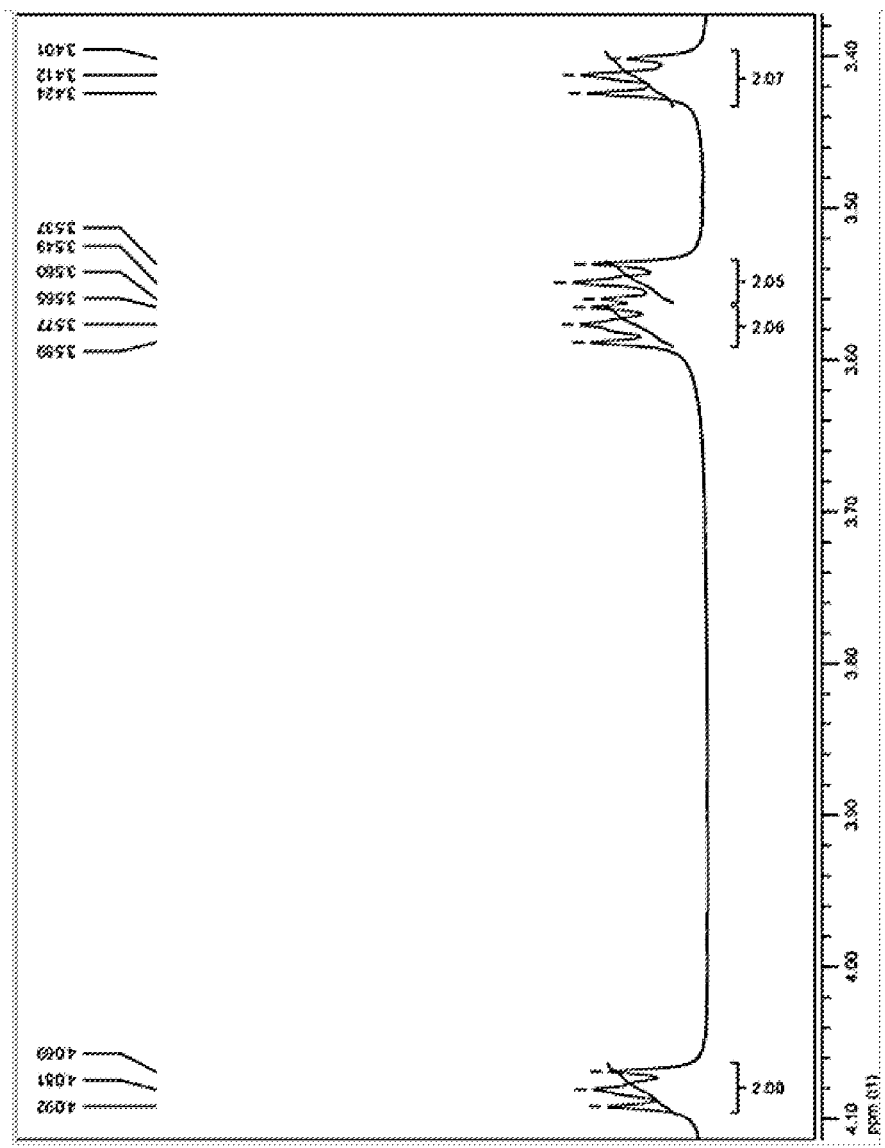
FIG. 3B illustrates a magnified $^1$H NMR spectrum of 5-tosyloxy-3-oxapentanol, consistent with one or more exemplary embodiments of the present disclosure.

FIG. 3A illustrates a proton nuclear magnetic resonance ($^1$H NMR) spectrum of 5-tosyloxy-3-oxapentanol, consistent with one or more exemplary embodiments of the present disclosure. Referring to FIG. 3A, the $^1$H NMR spectrum was consistent with a structure of the 5-tosyloxy-3-oxapentanol. $^1$HNMR (400 MHZ, CDCl3)=δ 2.34 (s, 3H), 2.88 (s, 1H), 3.40 (t, J=4.4 Hz, 2H), 3.53 (t, J=4.4 Hz, 2H), 3.56 (t, J=4.8 Hz, 2H), 4.06 (t, J=4.8 Hz, 2H), 7.25 (d, J=8.4 Hz, 2H), 7.67 (d, J=8.4 Hz, 2H). Also, presence of a peak at 2.88 ppm in the $^1$H NMR spectrum of the 5-tosyloxy-3-oxapentanol indicates that only one hydroxyl (OH) group of the diethylene glycol was involved in the reaction and replaced with a tosyl group. The other OH group of the diethylene glycol remained intact after reacting the diethylene glycol with the p-toluenesulfonyl chloride. FIG. 3B illustrates a magnified $^1$H NMR spectrum of 5-tosyloxy-3-oxapentanol, consistent with one or more exemplary embodiments of the present disclosure. Referring to FIG. 3B, the magnified $^1$H NMR spectrum of the aliphatic region of the 5-tosyloxy-3-oxapentanol, is shown.

Figure 4:
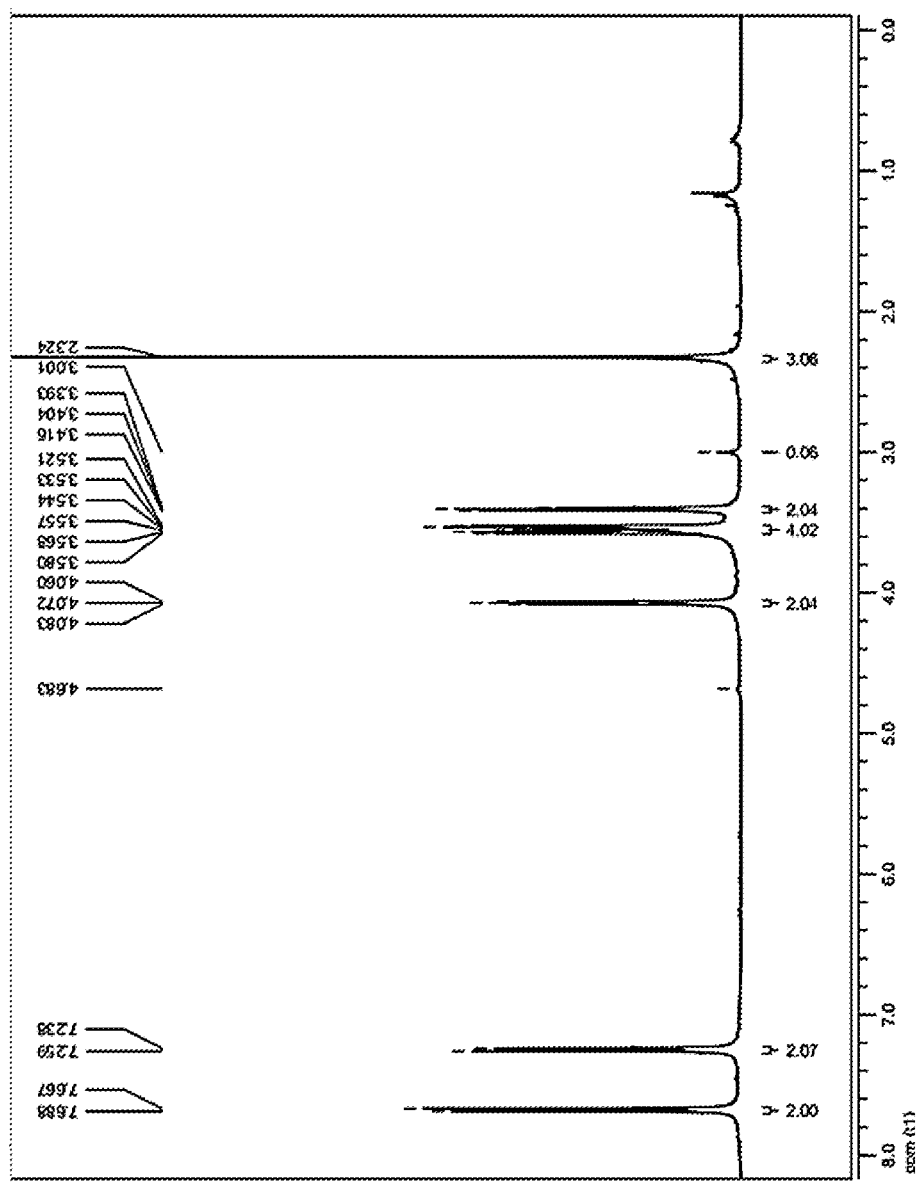
FIG. 4 illustrates a $^1$H NMR spectrum of 5-tosyloxy-3-oxapentanol exchange with $D_2O$, consistent with one or more exemplary embodiments of the present disclosure.

In order to provide further confirmation that one OH group of the diethylene glycol remained intact while forming the 5-tosyloxy-3-oxapentanol, $D_2O$ was added to a NMR tube containing the 5-tosyloxy-3-oxapentanol and deuterated chloroform ($CDCl_3$) to conduct a reaction between deuterium and hydrogen of the intact OH group. FIG. 4 illustrates a $^1$H NMR spectrum of 5-tosyloxy-3-oxapentanol exchange with $D_2O$, consistent with one or more exemplary embodiments of the present disclosure. Referring to FIGS. 3A-4, the $^1$H NMR spectrum of 5-tosyloxy-3-oxapentanol exchange with $D_2O$ lacks a peak at 3 ppm compared to the H NMR spectrum of the 5-tosyloxy-3-oxapentanol; therefore, the 5-tosyloxy-3-oxapentanol contained a hydroxyl group from the diethylene glycol, which remained intact and could be reacted with deuterium of the $D_2O$.

Figure 5:
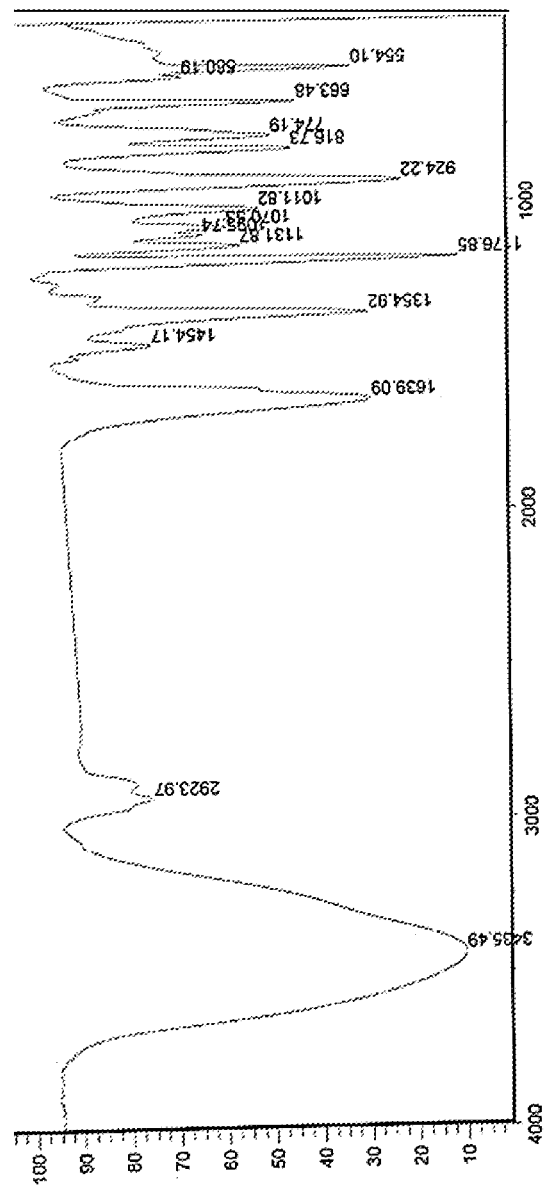
FIG. 5 illustrates a Fourier-transform infrared (FTIR) spectrum of 5-tosyloxy-3-oxapentanol, consistent with one or more exemplary embodiments of the present disclosure.

FIG. 5 illustrates a Fourier-transform infrared (FTIR) spectrum of 5-tosyloxy-3-oxapentanol, consistent with one or more exemplary embodiments of the present disclosure. Referring to FIG. 5, the FTIR spectrum of 5-tosyloxy-3-oxapentanol exhibited peaks at wavelengths 3435 $cm^{-1}$, 2923 $cm^{-1}$, 1639 $cm^{-1}$, 1454 $cm^{-1}$, 1354 $cm^{-1}$, 1176 $cm^{-1}$, 1070 $cm^{-1}$, 1011 $cm^{-1}$, and 774 $cm^{-1}$ which may be attributed to the structure of the exemplary 5-tosyloxy-3-oxapentanol. Also, the broad peak at the wavelength of about 3435 $cm^{-1}$ indicates the presence of a hydroxyl group in the structure of the tosyloxy-3-oxapentanol.

Example 2: Producing 2-(2-Phthalimidoethoxy) Ethanol Using 5-Tosyloxy-3-Oxapentanol In this example, 2-(2-phthalimidoethoxy) ethanol was produced by reacting 5-tosyloxy-3-oxapentanol with potassium phthalate utilizing a process similar to step 104 of exemplary method 100 as presented in FIG. 1. At first, a mixture containing potassium phthalimide was formed by mixing a solution phthalimide with a concentration of about 0.23 M with a solution of potassium hydroxide with a concentration of about 4.8 M for a time period of about 15 minutes in room temperature. The solution of phthalimide was formed by refluxing phthalimide with an amount of about 3.4 mmol in absolute ethanol with a volume of about 15 ml for a time period of about 30 minutes in a round bottom flask. The solution of potassium hydroxide was formed by mixing potassium hydroxide with an amount of about 3.5 mmoles to a mixture of ethanol with a volume of about 0.55 ml and distilled water with a volume of about 0.18 ml. In the end, the mixture containing the potassium phthalimide was filtered using a filter paper and washed with about 100 ml of hot acetone. Potassium phthalimide with an amount of about 0.49 g was obtained. The yield of the reaction was about 78%.

Figure 6:
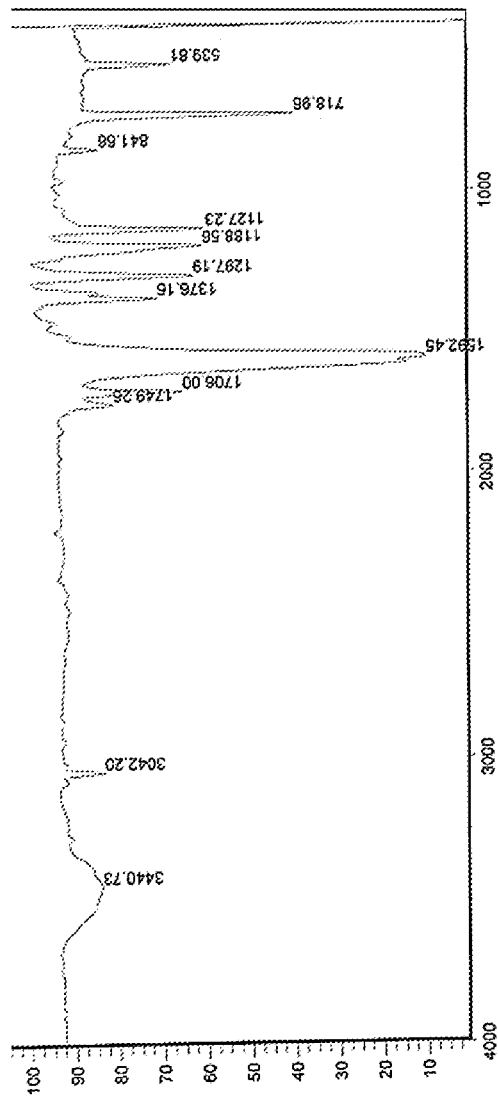
FIG. 6 illustrates an FTIR spectrum of potassium phthalimide, consistent with one or more exemplary embodiments of the present disclosure.

FIG. 6 illustrates an FTIR spectrum of potassium phthalimide, consistent with one or more exemplary embodiments of the present disclosure. Referring to FIG. 6, the FTIR spectrum of potassium phthalimide exhibited peaks at wavelengths 3440 $cm^{-1}$, 3042 $cm^{-1}$, 1749 $cm^{-1}$, 1706 $cm^{-1}$, 1592 $cm^{-1}$, 1376 $cm^{-1}$, and 1297 $cm^{-1}$ which may be attributed to the structure of potassium phthalimide.

In the next step, in order to produce the 2-(2-phthalimidoethoxy) ethanol, a reaction mixture was formed by adding the 5-tosyloxy-3-oxapentanol with an amount of about 0.9 mmol and the potassium phthalate with an amount of about 1.8 mmoles to dry DMF with a volume of about 6 ml. Then, the reaction mixture was refluxed at a temperature of about 180° C. for a time period of about 20 hours in a nitrogen atmosphere. The reaction progress was checked by thin-layer chromatography (TLC).

After refluxing the reaction mixture, a residue was formed by evaporating the DMF under reduced pressure. The residue was dissolved in water with a volume of about 10 ml, and a portion of a first organic phase was extracted by adding chloroform with a volume of about 200 ml (10*20 ml) in a decanter. Then, the obtained aqueous phase was saturated with sodium chloride. A remaining portion of the first organic phase was extracted by adding chloroform with a volume of about 75 ml (5*15 ml) to the decanter. The portions of the first organic phase were combined and dried over anhydrous magnesium sulfate utilizing a rotary evaporator. In the end, the 2-(2-phthalimidoethoxy) ethanol was purified by column chromatography on silica gel using a solution including n-hexane and ethyl acetate with a ratio of about 3:7. As a result, 2-(2-phthalimidoethoxy) ethanol with an amount of about 0.115 gram was obtained with a yield of about 55%.

Figure 7A:
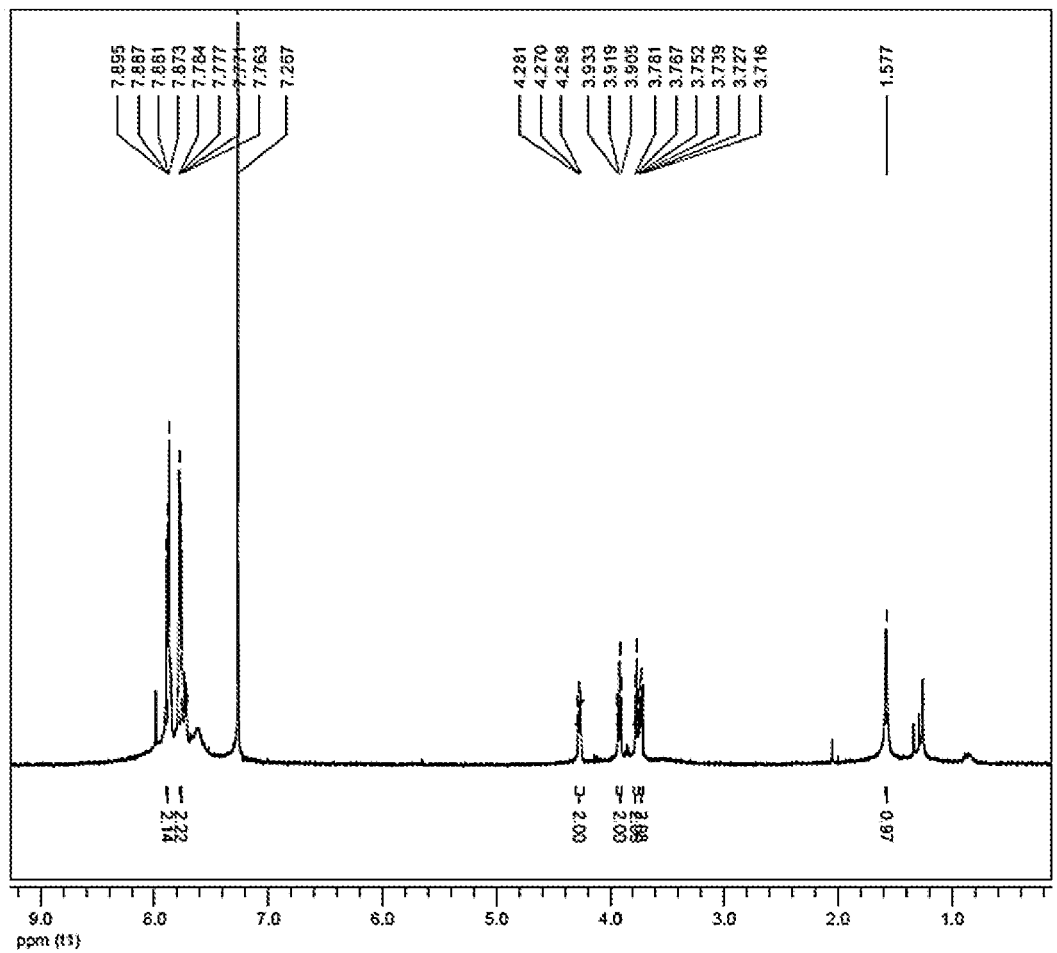
FIG. 7A illustrates a $^1$H NMR spectrum of 2-(2-phthalimidoethoxy) ethanol, consistent with one or more exemplary embodiments of the present disclosure.
Figure 7B:
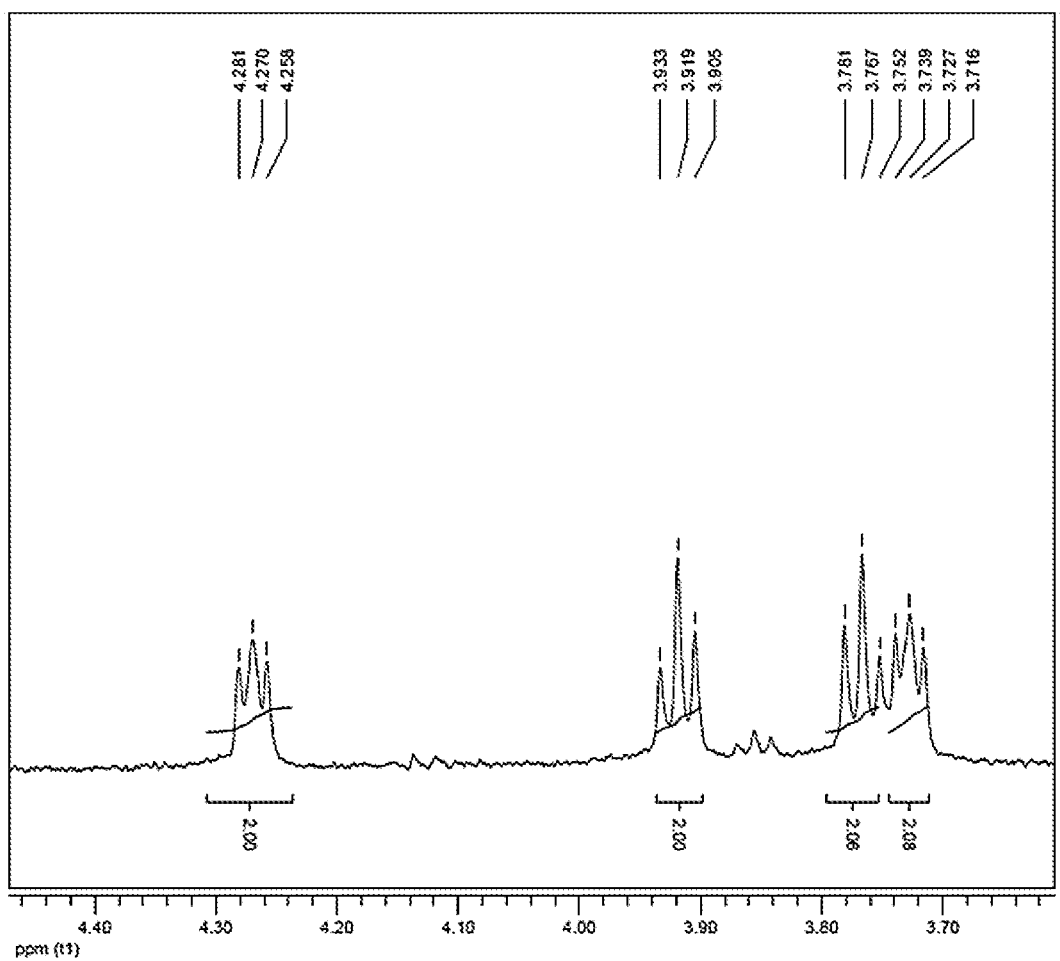
FIG. 7B illustrates a magnified $^1$H NMR spectrum of 2-(2-phthalimidoethoxy) ethanol, consistent with one or more exemplary embodiments of the present disclosure.

FIG. 7A illustrates a $^1$H NMR spectrum of 2-(2-phthalimidoethoxy) ethanol, consistent with one or more exemplary embodiments of the present disclosure. FIG. 7B illustrates a magnified $^1$H NMR spectrum of 2-(2-phthalimidoethoxy) ethanol, consistent with one or more exemplary embodiments of the present disclosure. Referring to FIGS. 7A-7B, the $^1$H NMR spectrum was consistent with a structure of the 2-(2-phthalimidoethoxy) ethanol. $^1$HNMR (400 MHZ, $CDCl_3$)=δ 1.58 (s, 1H), 3.71 (t, J=4.4 Hz, 2H), 3.75 (t, J=5.6 Hz, 2H), 3.91 (t, J=5.6 Hz, 2H), 4.25 (t, J=4.4 Hz, 2H), 7.76-7.78 (m, 2H), 7.87-7.89 (m, 2H). Also, the presence of a peak at 1.58 ppm in the $^1$H NMR spectrum of the 2-(2-phthalimidoethoxy) ethanol indicates that the tosyl group of the 5-tosyloxy-3-oxapentanol was replaced with the phthalimide group of the potassium phthalate and the OH group of the 5-tosyloxy-3-oxapentanol was intact. The OH group was present in the structure of the 2-(2-phthalimidoethoxy) ethanol. Referring again to FIG. 7B, the magnified $^1$H NMR spectrum of the aliphatic region of the 2-(2-phthalimidoethoxy) ethanol is shown.

Figure 8:
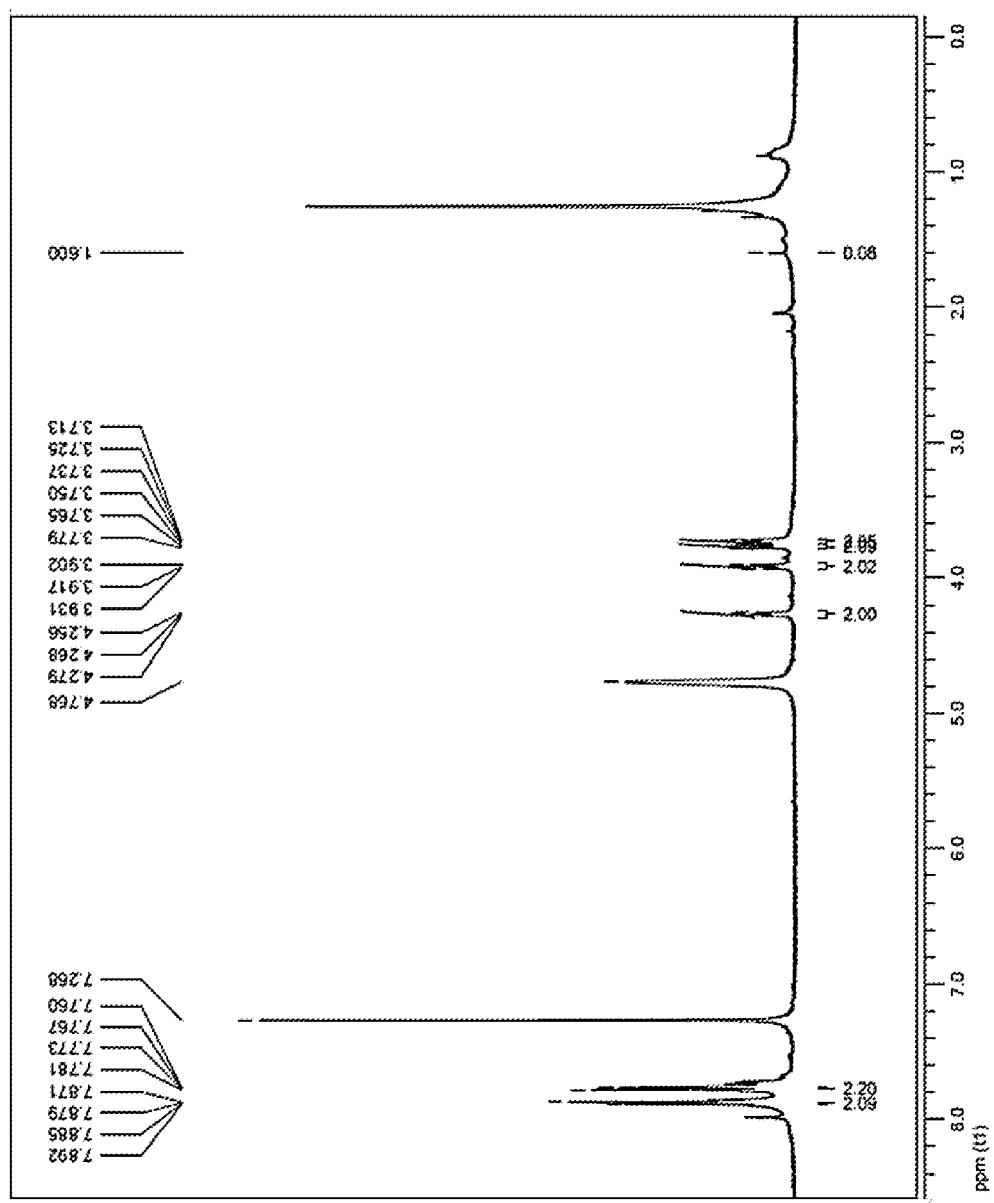
FIG. 8 illustrates a $^1$H NMR spectrum of 2-(2-phthalimidoethoxy) ethanol exchange with $D_2O$, consistent with one or more exemplary embodiments of the present disclosure.

In order to provide further confirmation that one OH group of the 5-tosyloxy-3-oxapentanol was intact during forming the 2-(2-phthalimidoethoxy) ethanol, the $D_2O$ was added to a NMR tube containing the 2-(2-phthalimidoethoxy) ethanol and $CDCl_3$ to conduct a reaction between deuterium and hydrogen of the presumed intact OH group. FIG. 8 illustrates a $^1$H NMR spectrum of 2-(2-phthalimidoethoxy) ethanol exchange with $D_2O$, consistent with one or more exemplary embodiments of the present disclosure. Referring to FIGS. 7A-8, the $^1$H NMR spectrum of the 2-(2-phthalimidoethoxy) ethanol exchange with $D_2O$ lack a peak at 1.60 ppm compared to the $^1$H NMR spectrum of the 2-(2-phthalimidoethoxy) ethanol; therefore, the 2-(2-phthalimidoethoxy) ethanol contained an intact hydroxyl group which could be reacted with deuterium of the $D_2O$.

Figure 9:
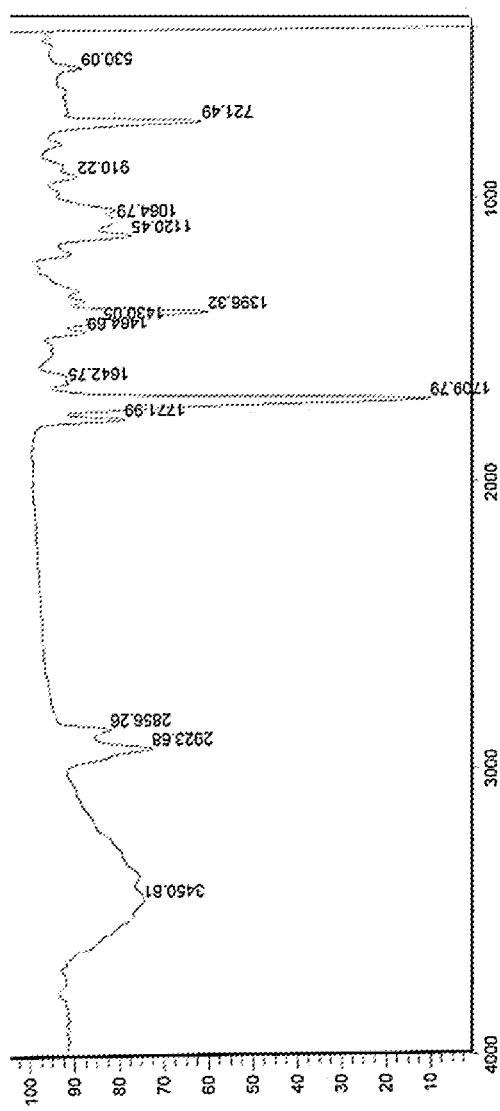
FIG. 9 illustrates an FTIR spectrum of 2-(2-phthalimidoethoxy) ethanol, consistent with one or more exemplary embodiments of the present disclosure.

FIG. 9 illustrates an FTIR spectrum of 2-(2-phthalimidoethoxy) ethanol, consistent with one or more exemplary embodiments of the present disclosure. Referring to FIG. 9, the FTIR spectrum of 2-(2-phthalimidoethoxy) ethanol exhibited peaks at wavelengths 3450 $cm^{-1}$, 2923 $cm^{-1}$, 2856 $cm^{-1}$, 1771 $cm^{-1}$, 1709 $cm^{-1}$, 1396 $cm^{-1}$, 1120 $cm^{-1}$, and 1064 $cm^{-1}$ which may be attributed to the structure of 2-(2-phthalimidoethoxy) ethanol. Also, the broad peak at the wavelength of about 3435 cm$^{-1}$ indicates the presence of a hydroxyl group in the structure of the 2-(2-phthalimidoethoxy) ethanol.

Example 3: Converting 2-(2-Phthalimidoethoxy) Ethanol to 2-(2-Aminoethoxy) Ethanol In this example, the 2-(2-aminoethoxy) ethanol was synthesized by reacting the 2-(2-phthalimidoethoxy) ethanol with hydrazine monohydrate utilizing a process similar to step 106 of exemplary method 100 as presented in FIG. 1. At first, a final mixture was formed by adding hydrazine monohydrate with an excess volume of about 0.82 ml to a solution of 2-(2-phthalimidoethoxy) ethanol. The solution of 2-(2-phthalimidoethoxy) ethanol was formed by dissolving 0.26 mmoles of 2-(2-phthalimidoethoxy) ethanol in absolute ethanol with a volume of about 6 ml. In the next step, the final mixture was refluxed at a temperature of about 90° C. for a time period of about 24 hours in a nitrogen atmosphere. The reaction progress was checked using TLC.

After refluxing the final mixture, the final mixture containing the 2-(2-aminoethoxy) ethanol was cooled to room temperature, and the 2-(2-aminoethoxy) ethanol was extracted from the final mixture. Extraction of the 2-(2-aminoethoxy) ethanol from the final mixture was done using chloroform, which separated the 2-(2-aminoethoxy) ethanol from the final mixture by precipitating different byproducts such as different compounds derived from the 2-(2-phthalimidoethoxy) ethanol.

In order to extract the 2-(2-aminoethoxy) ethanol from the final mixture, an extraction mixture was formed by adding 5 ml of chloroform to the final mixture and filtering the extraction mixture. Then, a residue was obtained by evaporating the absolute ethanol from the filtrate utilizing a rotary evaporator. Again, chloroform with a volume of about 5 ml was mixed with the residue for a time period of about 10 min and then filtered using a filter paper. The filtrate was evaporated utilizing a rotary evaporator. Adding the chloroform was repeated five times until no precipitate was formed when the chloroform was added to the residue.

In the end, In the end, the 2-(2-aminoethoxy) ethanol was purified by column chromatography on silica gel using a solution including n-hexane and ethyl acetate with a ratio of 3:7. As a result, the 2-(2-aminoethoxy) ethanol as a colorless oil with an amount of about 0.02 gram was obtained with a yield of about 74%. The overall yield of the method for synthesizing 2-(2-aminoethoxy) ethanol from diethylene glycol was about 33%.

Figure 10A:
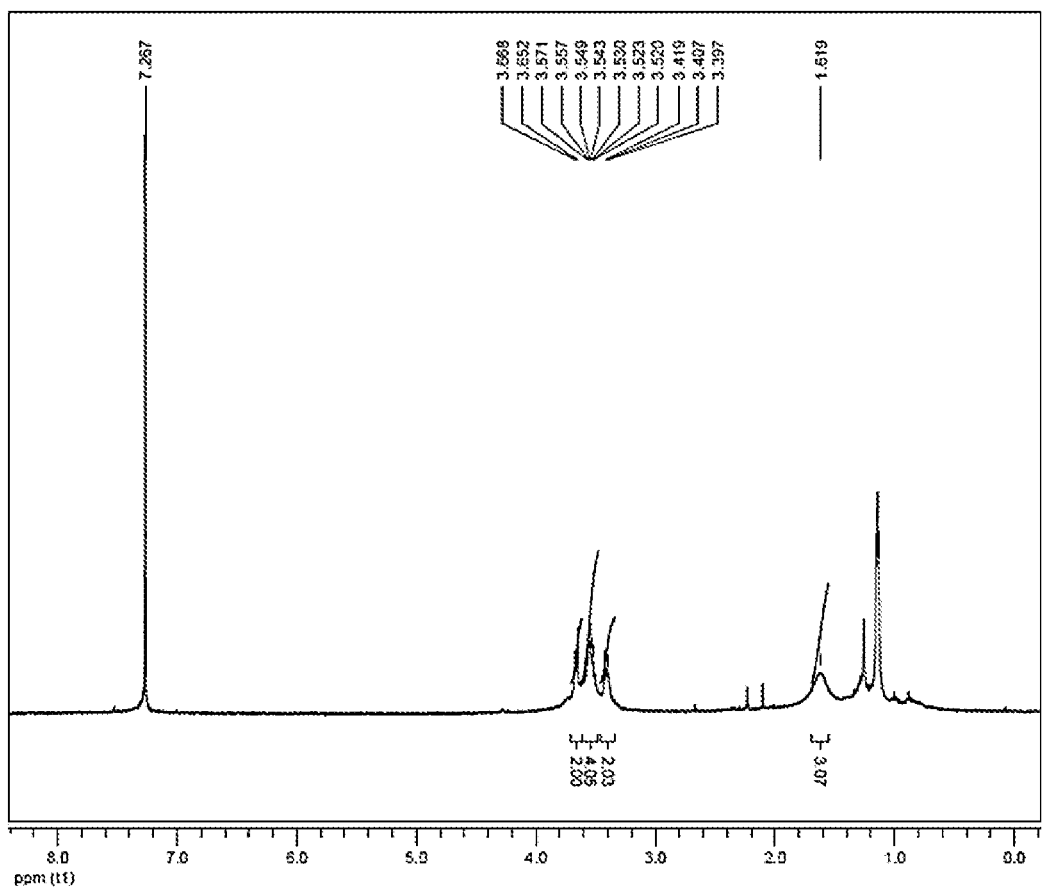
FIG. 10A illustrates a $^1$H NMR spectrum of 2-(2-aminoethoxy) ethanol, consistent with one or more exemplary embodiments of the present disclosure.
Figure 10B:
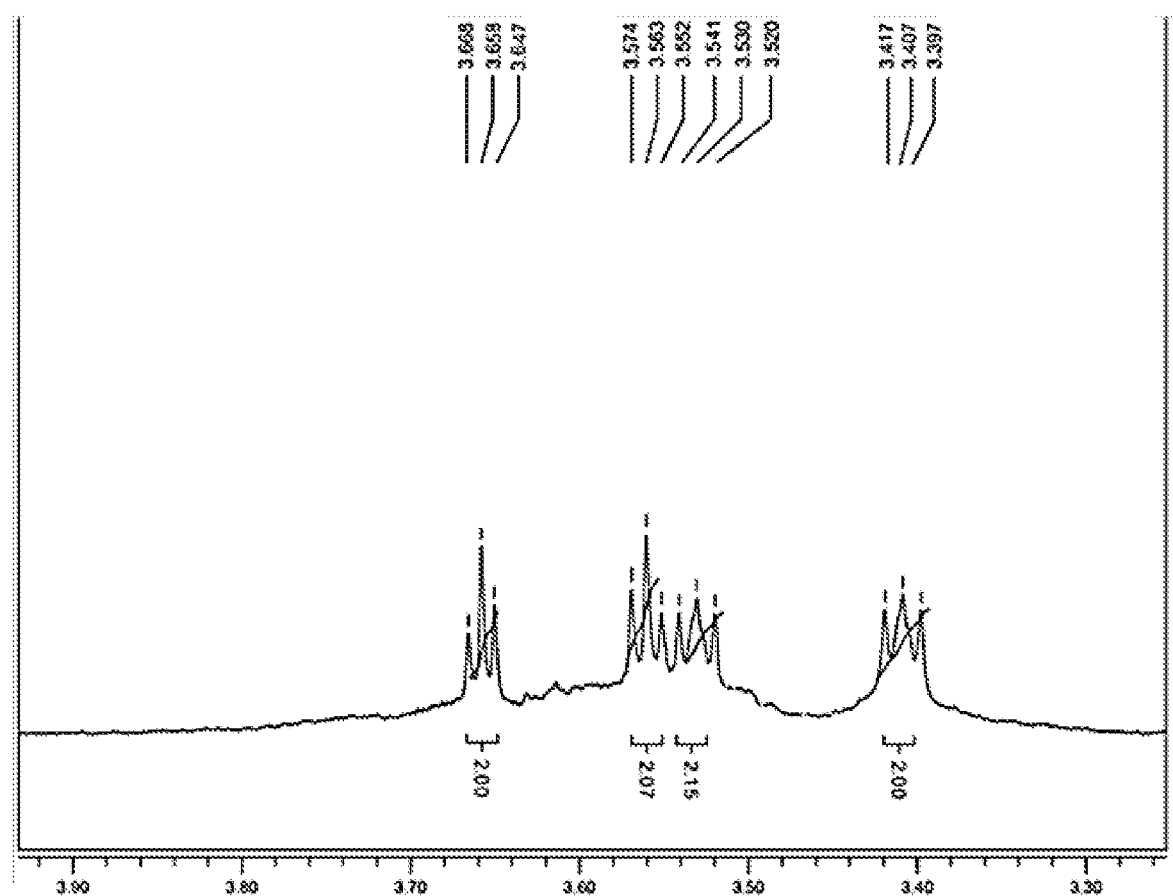
FIG. 10B illustrates a magnified $^1$H NMR spectrum of 2-(2-aminoethoxy) ethanol, consistent with one or more exemplary embodiments of the present disclosure.

FIG. 10A illustrates a $^1$H NMR spectrum of 2-(2-aminoethoxy) ethanol, consistent with one or more exemplary embodiments of the present disclosure. FIG. 10B illustrates a magnified $^1$H NMR spectrum of 2-(2-aminoethoxy) ethanol, consistent with one or more exemplary embodiments of the present disclosure. Referring to FIGS. 10A-10B, the $^1$H NMR spectrum was consistent with the proposed structure of 2-(2-aminoethoxy) ethanol. $^1$HNMR (400 MHZ, CDCl3) =δ 1.62 (brs, 3H), 3.39 (t, J=4.0 Hz, 2H), 3.52 (t, J=4.0 Hz, 2H), 3.55 (t, J=4.4 Hz, 2H), 3.64 (t, J=4.4 Hz, 2H). Also, the presence of a peak at 1.62 ppm in the $^1$H NMR spectrum of the 2-(2-aminoethoxy) ethanol indicates that the phthalimide group of the 2-(2-phthalimidoethoxy) ethanol participated in the reaction with hydrazine monohydrate and the OH group of the 2-(2-phthalimidoethoxy) ethanol was intact. The OH group was present in the structure of the 2-(2-aminoethoxy) ethanol. Referring again to FIG. 10B, the magnified $^1$H NMR spectrum of the aliphatic region of the 2-(2-aminoethoxy) ethanol is shown.

Figure 11:
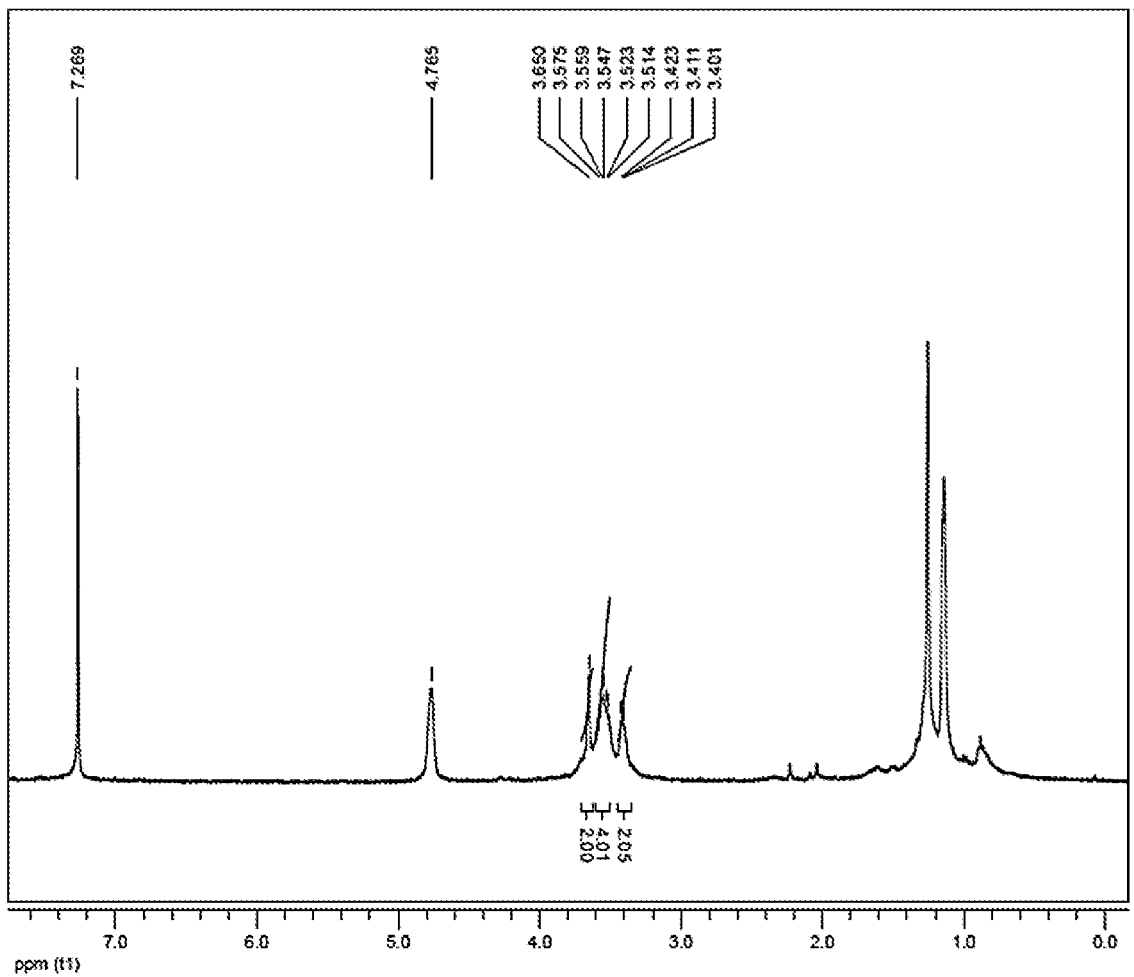
FIG. 11 illustrates a $^1$H NMR spectrum of 2-(2-aminoethoxy) ethanol exchange with $D_2O$, consistent with one or more exemplary embodiments of the present disclosure.

FIG. 11 illustrates a $^1$H NMR spectrum of 2-(2-aminoethoxy) ethanol exchange with D$_2$O, consistent with one or more exemplary embodiments of the present disclosure. Referring to FIG. 11, the $^1$H NMR spectrum of the 2-(2-aminoethoxy) ethanol exchange with D$_2$O lack peaks related to the hydrogen of the hydroxyl group and hydrogens of the amine group at 1.62 ppm compared to the $^1$H NMR spectrum of the 2-(2-aminoethoxy) ethanol; therefore, the 2-(2-aminoethoxy) ethanol contained hydrogens a hydroxyl group and amine group which could be reacted with deuterium of the D$_2$O.

Figure 12:
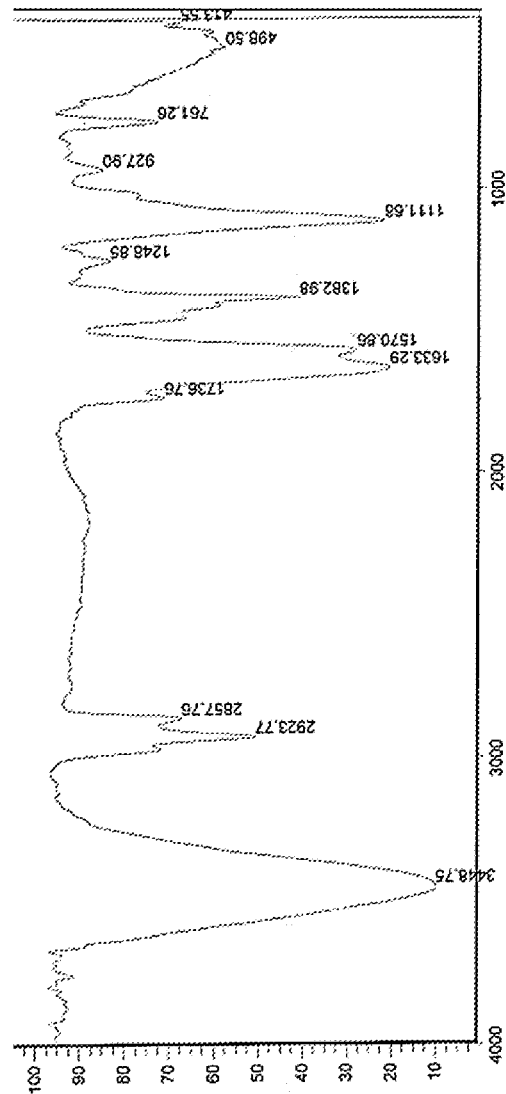
FIG. 12 illustrates an FTIR spectrum of 2-(2-aminoethoxy) ethanol, consistent with one or more exemplary embodiments of the present disclosure.

FIG. 12 illustrates an FTIR spectrum of 2-(2-aminoethoxy) ethanol, consistent with one or more exemplary embodiments of the present disclosure. Referring to FIG. 12, the FTIR spectrum of 2-(2-aminoethoxy) ethanol exhibited peaks at wavelengths 3448 cm$^{-1}$, 2923 cm$^{-1}$, 2857 cm$^{-1}$, 1633 cm$^{-1}$, 1570 cm$^{-1}$, 1382 cm$^{-1}$, 1111 cm$^{-1}$ which may be attributed to the structure of 2-(2-aminoethoxy) ethanol. Also, the broad peak at the wavelength of about 3448 cm$^{-1}$ indicates the presence of a hydroxyl group and amine groups in the structure of the 2-(2-aminoethoxy) ethanol.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A method for synthesizing 2-(2-aminoethoxy) ethanol, comprising:
   producing 2-(2-phthalimidoethoxy) ethanol by reacting 5-tosyloxy-3-oxapentanol with potassium phthalate, wherein reacting the 5-tosyloxy-3-oxapentanol with potassium phthalate comprises:
     refluxing a reaction mixture containing the 5-tosyloxy-3-oxapentanol and the potassium phthalate in dry dimethylformamide (DMF);
     extracting a first organic phase containing the 2-(2-phthalimidoethoxy) ethanol from the reaction mixture using a first portion of chloroform; and
     purifying the 2-(2-phthalimidoethoxy) ethanol from the first organic phase; and
   converting the 2-(2-phthalimidoethoxy) ethanol to the 2-(2-aminoethoxy) ethanol, comprising:
     forming a final mixture containing the 2-(2-aminoethoxy) ethanol by reacting the 2-(2-phthalimidoethoxy) ethanol with hydrazine monohydrate;
     extracting a second organic phase containing the 2-(2-aminoethoxy) ethanol from the final mixture using a second portion of chloroform; and
     purifying the 2-(2-aminoethoxy) ethanol from the second organic phase.

2. A method for synthesizing 2-(2-aminoethoxy) ethanol, comprising:
   producing 2-(2-phthalimidoethoxy) ethanol by reacting 5-tosyloxy-3-oxapentanol with potassium phthalate; and
   converting the 2-(2-phthalimidoethoxy) ethanol to the 2-(2-aminoethoxy) ethanol by reacting the 2-(2-phthalimidoethoxy) ethanol with hydrazine monohydrate,
   wherein reacting the 2-(2-phthalimidoethoxy) ethanol with the hydrazine monohydrate comprises:
     forming a final mixture by adding the hydrazine monohydrate to a solution of 2-(2-phthalimidoethoxy) ethanol;
     refluxing the final mixture in a nitrogen atmosphere;
     extracting a second organic phase containing the 2-(2-aminoethoxy) ethanol from the final mixture using a second portion of chloroform; and
     purifying the 2-(2-aminoethoxy) ethanol from the second organic phase.

3. The method of claim 2, wherein refluxing the final mixture in the nitrogen atmosphere comprises refluxing the final mixture in the nitrogen atmosphere for a time period between 20 hours and 26 hours.

4. The method of claim 2, wherein the solution of 2-(2-phthalimidoethoxy) ethanol has a concentration between 0.042 M and 0.045 M in absolute ethanol.

5. The method of claim 2, wherein adding the hydrazine monohydrate to the solution of the 2-(2-phthalimidoethoxy) ethanol comprises adding the hydrazine monohydrate with a volume concentration between 13% and 14.3% (v/v) to the solution of the 2-(2-phthalimidoethoxy) ethanol.

6. The method of claim 2, wherein refluxing the final mixture in the nitrogen atmosphere comprises refluxing the final mixture at a temperature between 170° C. and 190° C.

7. The method of claim 2, wherein extracting the 2-(2-aminoethoxy) ethanol from the final mixture using the second portion of chloroform comprises adding the second portion of chloroform to the final mixture at room temperature.

8. The method of claim 7, wherein adding the second portion of chloroform to the final mixture comprises adding the second portion of chloroform to the final mixture with a ratio of the 2-(2-phthalimidoethoxy) ethanol to the second portion of chloroform between 0.0100 mol/L and 0.0108 mol/L.

9. The method of claim 7, wherein adding the second portion of chloroform to the final mixture comprises adding the second portion of chloroform to the final mixture until no precipitate is formed in the final mixture.

10. The method of claim 2, wherein reacting the 5-tosyloxy-3-oxapentanol with the potassium phthalate comprises:
    forming a reaction mixture by adding the 5-tosyloxy-3-oxapentanol and the potassium phthalate to dry dimethylformamide (DMF);
    refluxing the reaction mixture in a nitrogen atmosphere;
    extracting a first organic phase containing the 2-(2-phthalimidoethoxy) ethanol from the reaction mixture using a first portion of chloroform; and
    purifying the 2-(2-phthalimidoethoxy) ethanol from the first organic phase.

11. The method of claim 10, wherein extracting the 2-(2-phthalimidoethoxy) ethanol from the reaction mixture using the first portion of chloroform comprises adding the first portion of chloroform to the reaction mixture at room temperature.

12. The method of claim 10, wherein refluxing the reaction mixture in the nitrogen atmosphere comprises refluxing the reaction mixture in the nitrogen atmosphere for a time period between 18 hours and 22 hours.

13. The method of claim 10, wherein adding the 5-tosyloxy-3-oxapentanol and the potassium phthalate to the dry DMF comprises adding the 5-tosyloxy-3-oxapentanol and the potassium phthalate to the dry DMF with a molar ratio of the 5-tosyloxy-3-oxapentanol to the potassium phthalate between 0.4 and 0.6.

14. The method of claim 10, wherein adding the 5-tosyloxy-3-oxapentanol and the potassium phthalate to the dry DMF comprises adding the 5-tosyloxy-3-oxapentanol with a concentration between 0.13 M and 0.17 M to the dry DMF.

15. The method of claim 10, wherein adding the 5-tosyloxy-3-oxapentanol and the potassium phthalate to the dry DMF comprises adding the potassium phthalate with a concentration between 0.28 M and 0.32 M to the dry DMF.

16. The method of claim 10, wherein refluxing the reaction mixture in the nitrogen atmosphere comprises refluxing the reaction mixture at a temperature between 85° C. and 95° C.

17. The method of claim 2 further comprising forming the 5-tosyloxy-3-oxapentanol by reacting p-toluenesulfonyl chloride with diethylene glycol.

18. The method of claim 2, wherein purifying the 2-(2-aminoethoxy) ethanol from the second organic phase comprises isolating the 2-(2-aminoethoxy) ethanol from the second organic phase using a column chromatography technique.

\* \* \* \* \*